United States Patent
Iyer et al.

(10) Patent No.: US 11,548,907 B2
(45) Date of Patent: Jan. 10, 2023

(54) METHOD FOR PRODUCING ALLULOSE CRYSTALS

(71) Applicant: Tate & Lyle Ingredients Americas LLC, Hoffman Estates, IL (US)

(72) Inventors: Krishnan Viswanathan Iyer, Champaign, IL (US); James Gaddy, Algonquin, IL (US); Jerry Lynn Turner, Shelbyville, IL (US); Brian Timothy Pohrte, St. Charles, IL (US)

(73) Assignee: Tate & Lyle Solutions USA LLC, Hoffman Estates, IL (US)

( * ) Notice: Subject to any disclaimer, the term of this patent is extended or adjusted under 35 U.S.C. 154(b) by 0 days.

(21) Appl. No.: 17/036,995

(22) Filed: Sep. 29, 2020

(65) Prior Publication Data
US 2021/0009619 A1 Jan. 14, 2021

Related U.S. Application Data

(62) Division of application No. 16/341,683, filed as application No. PCT/US2017/058753 on Oct. 27, 2017, now abandoned.

(60) Provisional application No. 62/414,280, filed on Oct. 28, 2016.

(51) Int. Cl.
*C07H 3/02* (2006.01)
*A23L 27/30* (2016.01)
*C07H 1/06* (2006.01)

(52) U.S. Cl.
CPC .............. *C07H 3/02* (2013.01); *A23L 27/33* (2016.08); *C07H 1/06* (2013.01); *C07B 2200/13* (2013.01)

(58) Field of Classification Search
CPC .. C07H 3/02; C07H 1/06; A23L 27/33; C07B 2200/13
USPC ......................................................... 536/124
See application file for complete search history.

(56) References Cited

U.S. PATENT DOCUMENTS

| | | | |
|---|---|---|---|
| 4,357,172 A | 11/1982 | Edwards | |
| 5,411,880 A | 5/1995 | Izumori et al. | |
| 8,030,035 B2 | 10/2011 | Oh et al. | |
| 8,524,888 B2 | 9/2013 | Lee et al. | |
| 8,735,106 B2 | 5/2014 | Hong et al. | |
| 10,246,476 B2 | 4/2019 | Kim et al. | |
| 2014/0370171 A1 | 12/2014 | Takaoka et al. | |
| 2015/0210996 A1 | 7/2015 | Woodyer et al. | |
| 2017/0313734 A1 | 11/2017 | Kim et al. | |
| 2018/0327796 A1 | 11/2018 | Lee et al. | |
| 2019/0246673 A1* | 8/2019 | Park .................. | A23L 27/72 |

FOREIGN PATENT DOCUMENTS

| | | | |
|---|---|---|---|
| CN | 101109021 A | | 1/2008 |
| CN | 102250157 A | | 11/2011 |
| EP | WO 2016/012854 | * | 1/2016 |
| EP | 3210478 A1 | | 8/2017 |
| JP | 05277000 A | | 10/1993 |
| JP | 2001206054 A | | 7/2001 |
| JP | 2005006520 A | | 1/2005 |
| TW | 201332455 A | | 8/2013 |
| WO | 2011119004 A2 | | 9/2011 |
| WO | 2015075473 | | 5/2015 |
| WO | 2016012854 A1 | | 1/2016 |
| WO | 2016064087 A1 | | 4/2016 |
| WO | 2016135458 A1 | | 9/2016 |

OTHER PUBLICATIONS

Taiwan Office Action with Search Report for Taiwan Application No. 106137167, dated Jul. 22, 2021, 9 pages.
International Preliminary Report on Patentability for International Application No. PCT/US2017/058753, dated Apr. 30, 2019, 9 pages.
International Search Report and Written Opinion for International Application No. PCT/US2017/058753, dated May 22, 2018, 15 pages.
Entire patent prosecution history of U.S. Appl. No. 16/341,683, filed Apr. 12, 2019 entitled, "Method for Producing Allulose Crystals."
Japanese Notice of Reasons for Rejection for Japanese Application No. 2019-520948, dated Nov. 8, 2021 with translation, 7 pages.
Israeli Office Action for Application No. 289910, dated Aug. 8, 2022, 4 pages.
Chinese Office Action for Chinese Application No. 201780066740.7, dated Aug. 1, 2022, with translation, 19 pages.
Australian Examination Report for Australian Application No. 2021221889, dated Nov. 17, 2022, 4 pages.
Australian Examination Report for Australian Application No. 2021221893, dated Nov. 17, 2022, 4 pages.

* cited by examiner

*Primary Examiner* — Yih-Horng Shiao
(74) *Attorney, Agent, or Firm* — RatnerPrestia

(57) ABSTRACT

Allulose crystals are efficiently produced from an allulose syrup using seed crystals.

23 Claims, 2 Drawing Sheets

METHOD FOR PRODUCING ALLULOSE CRYSTALS

CROSS-REFERENCE TO RELATED APPLICATIONS

This is a Divisional Application of U.S. application Ser. No. 16/341,683, filed Apr. 12, 2019, which is the U.S. National Phase of International Application No PCT/US2017/058753, filed Oct. 27, 2017, which claims priority to United States Provisional Patent Application No. 62/414,280, filed Oct. 28, 2016, the disclosures of each of which are incorporated herein by reference herein in their entirety for all purposes.

FIELD OF THE INVENTION

The present invention relates to the production of crystals of allulose from syrups containing allulose.

DISCUSSION OF THE RELATED ART

Many food and beverage products contain nutritive sweeteners such as sucrose (generally referred to as 'sugar' or 'table sugar'), glucose, fructose, corn syrup, high fructose corn syrup and the like. Although desirable in terms of taste and functional properties, excess intake of nutritive sweeteners, such as sucrose, has long been associated with an increase in diet-related health issues, such as obesity, heart disease, metabolic disorders and dental problems. This worrying trend has caused consumers to become increasingly aware of the importance of adopting a healthier lifestyle and reducing the level of nutritive sweeteners in their diet.

In recent years, there has been a movement towards the development of replacements for nutritive sweeteners, with a particular focus on the development of low or zero-calorie sweeteners. One proposed alternative to nutritive sweeteners is allulose (also known as D-psicose). Allulose is known as a "rare sugar", since it occurs in nature in only very small amounts. It is about 70% as sweet as sucrose, but provides only around 5% of the calories of sucrose (approximately 0.2 kcal/g). It may therefore essentially be considered to be a 'zero calorie' sweetener.

In view of its scarcity in nature, production of allulose relies on the epimerization of readily available fructose. Ketose-3-epimerases can interconvert fructose and allulose, and various ketose-3-epimerases are known for carrying out this conversion. Such epimerization reactions are typically conducted using an aqueous medium in which fructose is initially dissolved, wherein the allulose-containing product obtained as a result of the epimerization is in the form of a solution of allulose in water. Further processing and purification of the reaction product may be conducted in accordance in known procedures, whereby an allulose syrup containing allulose in fairly high concentration and purity is produced. Such allulose syrups are capable of being used in many consumable products, including foods and beverages, as substitutes for conventional "sugar" syrups such as glucose syrups, high fructose corn syrups and the like.

For other applications, however, it would be desirable to utilize allulose which is in "dry," free-flowing, crystalline form, i.e., a form generally resembling that of table sugar. Although some attempts to develop procedures for producing crystalline allulose have been reported (see, for example, U.S. Pat. No. 8,524,888 and WO 2016/064087), it is generally recognized that allulose is a saccharide which is challenging to crystallize in a controlled, efficient way such that crystals of suitable shape and size are reliably obtained in high yield. Therefore, improved crystallization methods for allulose are still of great interest.

SUMMARY OF THE INVENTION

Various aspects of the present invention may be summarized as follows:

Aspect 1: A method for producing allulose crystals, wherein the method comprises:
 a) cooling and agitating a first admixture comprised of a first portion of allulose syrup and allulose seed crystals and initiating crystallization of allulose dissolved in the allulose syrup, thereby forming a first massecuite comprising allulose crystals and a first mother liquor containing residual dissolved allulose, the cooling and agitating being continued until a first preselected target yield of allulose crystals is achieved;
 b) optionally, separating the first massecuite into a first portion (which may be subjected to further processing steps, such as separating the allulose crystals from the mother liquor portion and washing and/or drying the separated allulose crystals) and a second portion;
 c) optionally, combining a second portion of allulose syrup with the second portion of the first massecuite to form a second admixture; and
 d) optionally, cooling and agitating the second admixture and initiating crystallization of allulose dissolved in the second portion of allulose syrup, thereby forming a second massecuite comprising allulose crystals and a second mother liquor containing residual dissolved allulose, the cooling and agitating being continued until a second preselected target yield of allulose crystals is achieved.

In various embodiments of Aspect 1, at least steps a) and b) are performed, at least steps a)-c) are performed, or at least steps a)-d) are performed.

Aspect 2: The method of Aspect 1, wherein the first admixture is obtained by combining the first portion of allulose syrup and dry allulose crystals.

Aspect 3: The method of Aspect 1, wherein the first admixture is obtained by combining with the first portion of allulose syrup and a heel comprised of allulose crystals and a mother liquor.

Aspect 4: The method of any of Aspects 1-3, wherein the first admixture and second admixture are agitated in steps a) and d), if step d) is performed, respectively using an agitator having a tip speed of 0.02 to 2 m/sec.

Aspect 5: The method of any of Aspects 1-4, wherein step a) additionally comprises, following initiation of crystallization of allulose dissolved in the allulose syrup, combining at least one additional portion of allulose syrup with the first admixture.

Aspect 6: The method of any of Aspects 1-5, wherein the cooling in step a) involves lowering the temperature of the first admixture from within an initial temperature range to within a second temperature range and holding the temperature of the first admixture within the second temperature range for a period of time.

Aspect 7: The method of any of Aspects 1-6, wherein step d) is performed and the cooling in step d) involves lowering the temperature of the second admixture from within an initial temperature range to within a second temperature range and holding the temperature of the second admixture within the second temperature range for a period of time.

Aspect 8: The method of any of Aspects 1-7, wherein the allulose syrup has a dry solids content of 70% to 95% by weight, 75% to 90% by weight, or 80% to 85% by weight.

Aspect 9: The method of any of Aspects 1-8, wherein the allulose syrup has an allulose purity of at least 70%, at least 75%, at least 80%, at least 85%, or at least 90%.

Aspect 10: The method of any of Aspects 1-9, comprising an additional step of separating allulose crystals from the first mother liquor in the first portion of the first massecuite.

Aspect 11: The method of Aspect 10, wherein the separating is carried out at least in part by one or more physical separation methods selected from the group consisting of centrifugation, filtration, decantation, membrane separation and combinations thereof.

Aspect 12: The method of Aspect 10 or 11, wherein allulose crystals separated from the first mother liquor are subjected to i) washing with at least one of water, an organic solvent, a blend of organic solvents, a blend of water and organic solvent(s) or an aqueous solution comprised of at least one carbohydrate (e.g., allulose); ii) drying; or a combination thereof.

Aspect 13: The method of any of Aspects 1-12, wherein steps b)-d) are performed and repeated at least once.

Aspect 14: A method for producing allulose crystals, wherein the method comprises:
  a). passing a feed syrup/recycled massecuite admixture, comprised of i) a feed syrup, comprising water and dissolved allulose, and ii) a recycled massecuite comprising allulose crystals and a recycled massecuite mother liquor containing dissolved allulose, wherein the feed syrup/recycled massecuite admixture has been cooled to within a first crystallization temperature range, through a first stage crystallization zone, while agitating the feed syrup/recycled massecuite admixture, maintaining the feed syrup/recycled massecuite admixture within the first crystallization temperature range and initiating crystallization of allulose dissolved in the feed syrup and recycled massecuite mother liquor, thereby forming a first massecuite comprising allulose crystals and a first mother liquor containing residual dissolved allulose, and withdrawing the first massecuite which has achieved a first preselected target yield from the first stage crystallization zone;
  b). optionally, cooling the first massecuite withdrawn from the first stage crystallization zone to within a second crystallization temperature range and transferring the first massecuite to a second stage crystallization zone;
  c). optionally, passing the first massecuite through the second stage crystallization zone while agitating the first massecuite, maintaining the first massecuite within the second crystallization temperature range and initiating crystallization of allulose dissolved in the first mother liquor, thereby forming a second massecuite comprising allulose crystals and a second mother liquor containing residual dissolved allulose, and withdrawing the second massecuite which has achieved a second preselected target yield from the second stage crystallization zone; and
  d). optionally, repeating steps b and c at least once to yield a final massecuite comprising allulose crystals and a final mother liquor.

In various embodiments of Aspect 14, at least steps a) and b) are performed, at least steps a)-c) are performed, or at least steps a)-d) are performed.

Aspect 15: The method of Aspect 14, wherein steps a)-d) are performed and comprising an additional step of separating the allulose crystals in at least a portion of the final massecuite from the final mother liquor.

Aspect 16: The method of Aspect 14 or 15, wherein steps a)-d) are performed and a portion of the final massecuite is used as the recycled massecuite.

Aspect 17: The method of any of Aspects 14-16, wherein the feed syrup/recycled massecuite admixture is obtained by mixing in a mixing vessel the feed syrup with the recycled massecuite comprised of allulose crystals and a recycled massecuite mother liquor containing dissolved allulose to provide the feed syrup/recycled massecuite admixture and transferring the feed syrup/recycled massecuite admixture from the mixing vessel into the first stage crystallization zone.

Aspect 18: The method of any of Aspects 14-17, wherein the first admixture and second admixture are agitated in steps a) and c), if step c) is performed, respectively using an agitator having a tip speed of 0.02 to 2 m/sec.

Aspect 19: The method of any of Aspects 14-18, wherein the allulose syrup has a dry solids content of 70% to 95% by weight, 75% to 90% by weight, or 80% to 85% by weight.

Aspect 20: The method of any of Aspects 14-19, wherein the allulose syrup has an allulose purity of at least 70%, at least 75%, at least 80%, at least 85%, or at least 90%.

Aspect 21: The method of Aspect 15, wherein the separating is carried out at least in part by one or more physical separation methods selected from the group consisting of centrifugation, filtration, decantation, membrane separation and combinations thereof.

Aspect 22: The method of Aspect 15 or 21, wherein allulose crystals separated from the final mother liquor are subjected to i) washing with at least one of water, an organic solvent, a blend of organic solvents, a blend of water and organic solvent(s) or an aqueous solution comprised of at least one carbohydrate (e.g., allulose); ii) drying; or a combination thereof.

Aspect 23: The method of any of Aspects 14-22, wherein the feed syrup/recycled massecuite admixture is passed through the first stage crystallization zone in a plug flow manner and/or, if steps b) and c) are performed, the first massecuite is passed through the second stage crystallization zone in a plug flow manner.

Aspect 24: The method of any of Aspects 1-23, wherein the method is performed in a continuous manner.

Aspect 25: Allulose crystals, obtained in accordance with the method of any of Aspects 1-24.

Aspect 26: A consumable product, comprised of or prepared using allulose crystals in accordance with Aspect 25 and at least one additional ingredient other than allulose crystals.

Aspect 27: A method of making a consumable product, comprising using allulose crystals in accordance with Aspect 25.

Aspect 28: A mother liquor, obtained in accordance with the method of any of Aspects 1-24.

Aspect 29: The mother liquor of Aspect 28, wherein the mother liquor is suitable for use as a product consumable by humans or animals or as an ingredient in a formulated product consumable by humans or animals.

DETAILED DESCRIPTION OF CERTAIN EMBODIMENTS OF THE INVENTION

Allulose Syrup

Figure 1:
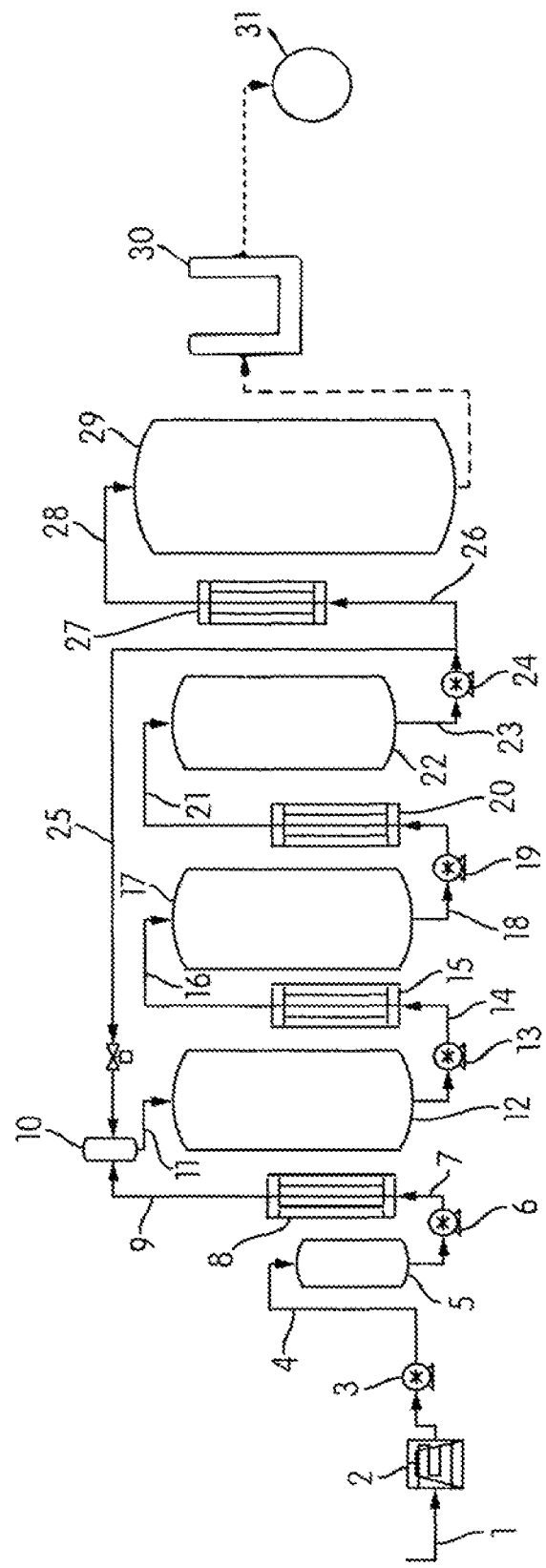
FIG. 1 illustrates in schematic form a crystallization system and process in accordance with one embodiment of the invention.

The present invention utilizes at least one allulose syrup as a starting material for a crystallization process, wherein allulose present in dissolved form in the syrup is converted to crystalline form. Methods of obtaining allulose syrups are well known in the art and are described, for example, in the following patent documents, the disclosure of each of which is incorporated herein by reference in its entirety for all purposes: WO 2016/135458; US 2015/0210996; U.S. Pat. Nos. 5,411,880; 8,735,106; and 8,030,035.

For example, the allulose syrup may be prepared by a process comprising contacting an aqueous solution of fructose with an allulose (D-psicose) epimerase enzyme under conditions effective to convert at least a portion of the fructose to allulose, purifying the reaction product obtained, and then concentrating the purified reaction product to a desired dry solids content. The purification steps may involve the removal of impurities from the reaction product using one or more techniques such as deproteination, decolorization (treatment with decolorizing agent(s)), desalting, ion exchange chromatography (using one or more ion exchange resins, such as anion exchange resin, cation exchange resin and the like), column chromatography, fractionation, and the like.

The allulose syrup should have a dry solids content which is sufficient to effect crystallization of allulose when the syrup is cooled in the presence of seed crystals, as described hereafter in more detail. For example, in various embodiments, the dry solids content of the allulose syrup may be at least 50% by weight, at least 55% by weight, at least 60% by weight, at least 65% by weight, at least 70% by weight, at least 75% by weight or at least 80% by weight. However, it will generally be preferred that the dry solids content of the allulose be sufficiently low that the syrup remains a free-flowing solution in the absence of seed crystals at the temperature at which the syrup is to be maintained prior to the initiation of crystallization by the introduction of seed crystals. Thus, in various embodiments of the invention, the allulose syrup has a dry solids content not greater than 90% or not greater than 85%. The desired dry solids content may be attained by subjecting a diluted allulose solution to an evaporation or concentration procedure wherein volatiles (e.g., water) are removed from the solution, leaving behind a more concentrated syrup. The evaporation/condensation conditions may advantageously be selected so as to minimize or reduce the extent of allulose degradation; for example, relatively low evaporation temperatures may be employed.

The purity of the allulose syrup may vary, but typically it will be desirable for allulose to constitute the majority, by weight, of the non-volatile substances present in the allulose syrup. Accordingly, the allulose purity of the syrup may be, in various embodiments of the invention, at least 60% by weight, at least 65% by weight, at least 70% by weight, at least 75% by weight, at least 80% by weight, at least 85% by weight or at least 90% by weight. The term "allulose purity" as used herein with respect to an allulose syrup means the percent by weight of allulose in the syrup, based on the total weight of dry solids in the syrup.

Seed Crystals of Allulose

The present invention employs seed crystals of allulose to help promote the initiation of crystallization of additional allulose from solution (e.g., the formation of solid crystals containing allulose that had previously been in solution in an allulose syrup, mother liquor or the like). In certain embodiments, the allulose seed crystals are in dry form (for example, dry crystals of allulose recovered from a previously performed crystallization) and/or in the form of a heel, such as a portion of a massecuite comprised of allulose crystals and a mother liquor. The precise amount of allulose seed crystals is not believed to be particularly critical, but may, for example, be employed in a quantity representing from about 0.1 to about 5% of the total amount of allulose present in a crystallization vessel or crystallization zone, as will be described in more detail subsequently. Generally speaking, allulose seed crystals of relatively high purity are preferred for use; for example, the allulose seed crystals may have an allulose purity of at least 90%, at least 95% or at least 99% by weight, in various embodiments of the invention. The term "allulose purity" as used herein with respect to allulose crystals means the percent by weight of allulose in the crystals, based on the total weight of dry solids in the crystals.

Description of Various Exemplary Embodiments of Crystallization Process

In one embodiment of the invention, batch crystallization of allulose may be performed in a jacketed vessel equipped with an agitator by dropping the temperature of the cooling medium (e.g., water or other heat transfer liquid) in the jacket to lower the massecuite temperature and thereby drive crystallization. The following series of steps may be performed:

1. The vessel is partially filled with a suitable allulose syrup.
2. The temperature of the cooling medium is set at a desired initial temperature.
3. The agitator is started and set at an RPM effective to provide a desired tip speed.
4. The temperature of the allulose syrup in the vessel is lowered to a desired temperature, by varying the temperature of the cooling medium as appropriate.
5. A desired amount of seed crystals (e.g., dry seed crystals) is added to the vessel (this addition may be performed prior to the time the allulose syrup reaches the temperature referenced in step 2).
6. Mix the seed crystals and the allulose syrup, using an appropriate agitator tip speed. The agitator tip speed may be selected to minimize or avoid breakage of the seed crystals as well as the allulose crystals subsequently formed during crystallization. In certain embodiments, the agitator tip speed is higher during the initial mixing of the seed crystals with the allulose syrup than it is during the subsequent crystallization step(s).
7. The temperature of the allulose syrup/seed crystal admixture is then lowered to a desired temperature effective to achieve crystallization of a portion of the allulose dissolved in the allulose syrup. This temperature will vary, depending upon, for example, the concentration of allulose in the syrup, but typically will be not greater than about 40° C. and not less than about 0° C.
8. Crystallization is permitted to continue, with a suitable degree of agitation, until a desired yield of allulose crystals is achieved (this may be checked by periodically withdrawing a sample from the vessel and measuring the dry solids content of the mother liquor).

9. To achieve the desired yield of allulose crystals, the temperature of the massecuite may continue to be lowered, either continuously or in one or more stages.
10. Once the desired yield of allulose crystals is met, the massecuite is combined with an additional portion of allulose syrup (filling the vessel, for example). Steps 7-9 are then repeated.
11. Once the desired yield of allulose crystals is achieved following the introduction of the additional portion of allulose syrup into the vessel, a portion (e.g., approximately one-quarter to three-quarters) of the massecuite is removed from the vessel, with the remaining portion of the massecuite being retained in the vessel to serve as a source of seed crystals for a subsequent batch of massecuite. In this way, multiple batches of massecuite may be prepared.
12. The portion(s) of the massecuite withdrawn from the vessel may be subjected to one or more desired processing steps, such as separating the allulose crystals from the mother liquor by one or more physical separation methods selected from the group consisting of centrifugation, filtration, decantation, membrane separation and combinations thereof and then washing and/or drying the separated allulose crystals.

In another embodiment of the invention, the crystallization may be conducted in a continuous manner involving a plurality of stages (e.g., three or four stages). Such a process may be carried out using a system as illustrated in schematic form in FIG. 1 and as further explained as follows.

An allulose syrup of suitable purity is introduced through line 1 to evaporator 2, wherein the dry solids content of the syrup is increased to the desired level. The allulose syrup is then pumped (utilizing pump 3) through line 4 into allulose syrup feed hold-up tank 5. From tank 5, the allulose syrup is pumped (using pump 6) via line 7 and introduced into heat exchanger 8, wherein the temperature of the allulose syrup is adjusted to a desired value prior to being fed via line 9 to mix tank 10. In mix tank 10, the allulose syrup is combined, using vigorous mixing, with massecuite from crystallization zone 22, which is fed to mix tank 10 using line 25. An admixture of allulose syrup and massecuite (which serves as a source of seed crystals) is withdrawn from mix tank 10 and introduced into crystallization zone 12. Crystallization zone 12 may be within a suitable tank or other vessel equipped with an agitator. Any agitator of the type known in the art may be used; in particular, the agitator may be any of the types of mechanical devices recognized as being useful in agitating solution/seed crystal mixtures in a crystallization process may be utilized. In one embodiment, the agitator in the crystallization zone can bring about its agitating effect horizontally but not vertically. In order to prevent or reduce turbulent flow and destruction/breakage of the crystals formed during crystallization, the agitation can be preferably carried out at a low speed. The agitator may be configured and operated so as to prevent crystals of allulose from adhering to the wall(s) and/or the bottom of a vessel constituting crystallization zone 12. According to one aspect of the invention, the admixture of allulose syrup and massecuite is not subjected to concentration within crystallization zone 12. The allulose syrup/massecuite admixture may move through crystallization zone 12 in a plug flow manner, with the tip speed of the agitator being adjusted as appropriate to promote crystallization of allulose dissolved in the liquid phase of the admixture and to generate allulose crystals of the desired size and shape. In one embodiment, the process parameters are controlled such that the allulose syrup/massecuite admixture is passed, in a descending continuous flow, through a vessel comprising crystallization zone 12. The flow rate of the admixture through crystallization zone 12 and thus the residence time of the admixture in crystallization zone 12 are controlled such that the admixture exiting from crystallization zone 12 via line 14 has a desired content of allulose crystals (i.e., the desired yield of allulose crystals is achieved by the time the admixture is withdrawn from crystallization zone 12). In one embodiment, the temperature of the allulose syrup/massecuite admixture remains constant or essentially constant as the admixture passes through crystallization zone 12. For example, the temperature of the admixture may be controlled such that the admixture temperature at the point of introduction into crystallization zone 12 differs by no more than 5° C., no more than 4° C., no more than 3° C., no more than 2° C. or no more than 1° C. from the temperature of the admixture at the point where it exits or is withdrawn from crystallization zone 12.

The massecuite obtained from crystallization zone 12 is further cooled using heat exchanger 15 to a desired temperature (which may be, for example, about 1° C. to about 10° C. lower than the temperature of the massecuite as it exits from crystallization zone 12) and introduced into crystallization zone 17, via line 16. According to one embodiment of the invention, the massecuite obtained from crystallization zone 12 is not subjected to concentration before or after being introduced into crystallization zone 17. Crystallization zone 17 may be within a suitable tank or other vessel equipped with an agitator. The massecuite may move through crystallization zone 17 in a plug flow manner, with the tip speed of the agitator being adjusted as appropriate to promote crystallization of allulose still dissolved in the liquid phase (mother liquor) of the massecuite. The flow rate of the massecuite through crystallization zone 17 and thus the residence time of the admixture in crystallization zone 17 are controlled such that the admixture exiting from crystallization zone 17 via line 18 has a desired content of allulose crystals (i.e., the desired yield of allulose crystals is achieved by the time the massecuite is withdrawn from crystallization zone 17), with the desired content of allulose crystals being higher than that of the massecuite withdrawn from crystallization zone 12. The massecuite in crystallization zone 17 is not subjected to concentration, according to one embodiment of the invention.

The massecuite obtained from crystallization zone 17 is further cooled using heat exchanger 20 to a desired temperature (which may be, for example, about 1° C. to about 10° C. lower than the temperature of the massecuite as it exits from crystallization zone 17) and introduced into crystallization zone 22, via line 21. According to one embodiment of the invention, the massecuite obtained from crystallization zone 17 is not subjected to concentration before or after being introduced into crystallization zone 22. Crystallization zone 22 may be within a suitable tank or other vessel equipped with an agitator. The massecuite may move through crystallization zone 22 in a plug flow manner, with the tip speed of the agitator being adjusted as appropriate to promote crystallization of allulose still dissolved in the liquid phase (mother liquor) of the massecuite. The flow rate of the massecuite through crystallization zone 22 and thus the residence time of the admixture in crystallization zone 22 are controlled such that the admixture exiting from crystallization zone 22 via line 23 has a desired content of allulose crystals (i.e., the desired yield of allulose crystals is achieved by the time the massecuite is withdrawn from crystallization zone 22), with the desired content of allulose crystals being higher than that of the massecuite withdrawn from crystallization zone 17. The massecuite in crystallization zone 22 is not subjected to concentration, according to one embodiment of the invention.

If so desired, one or more additional crystallization zones (not illustrated) may be introduced, which is or are operated in a manner similar to that of crystallization zones 12, 17 and 22, wherein the massecuite exiting crystallization zone 22 is subjected to further cooling and crystallization. According to certain embodiments of the invention, such further processing is carried out without any concentration of the massecuite.

Once a massecuite having the desired final target yield of allulose crystals has been produced, a portion of it may be recycled and utilized as a source of seed crystals as previously mentioned (being conveyed via line 25 to mix tank 10) and the remaining portion may be passed through heat exchanger 27 and fed via line 28 to massecuite hold-up tank 29. The massecuite from massecuite hold-up tank 29 may be subjected to a separation of the allulose crystals from the mother liquor using centrifuge 30, with the resulting cake of allulose crystals then being washed before being dried in rotary dryer 31.

Generally speaking, it will be desirable to control the crystallization conditions such that the final massecuite (i.e., the massecuite from which allulose crystals will be recovered, involving separation from the mother liquor component of the massecuite) does not have an overly high content of allulose crystals, since a high allulose crystal concentration may tend to result in a massecuite which has a high viscosity and which is consequently difficult to further process. Accordingly, in various embodiments of the invention, the yield of allulose crystals in the final massecuite is not more than 60%, not more than 55%, not more than 50% or not more than 45%. At the same time, it is desirable for the allulose crystal yield which is achieved in the final massecuite to be sufficiently high so as to reduce production costs. Thus, in various embodiments, the yield of allulose crystals in the final massecuite is at least 20%, at least 25%, at least 30%, at least 35% or at least 40%.

The mother liquor(s) separated from allulose crystals in accordance with various embodiments of the invention may be further processed and/or used in different ways. For example, a mother liquor recovered from a separation step may be simply used as is (e.g., in solution or syrup form) as a source of allulose in preparing or formulating a consumable product. If so desired, the mother liquor may be subjected to one or more processing steps such as concentration (evaporation) and/or treatment to remove impurities (using adsorbents or the like). In still other embodiments, a recovered mother liquor may be recycled back into a crystallization process of the type described herein, thus serving as a source (in whole or in part) of an allulose syrup starting material. Prior to such recycling, the mother liquor may be subjected to one or more processing steps such as concentration and/or purification.

Further Processing of Allulose Crystals

In various embodiments of the present invention, the method may comprise one or more additional steps wherein the allulose crystals present in a massecuite, following separation from the mother liquor portion of the massecuite by centrifugation, filtration, decantation, membrane separation or other such physical separation method, are subjected to further processing. For example, allulose crystals as separated from a mother liquor typically have some amount of the mother liquor on the outer surface to the crystals. Because the mother liquor generally contains some amount of impurities (substances other than allulose), the purity of the recovered crystals may be improved by subjecting the separated allulose crystals to one or more washing steps, wherein one or more volumes of a suitable liquid are used to wash the crystals. The washing step(s) may be performed in any suitable manner using techniques known in the art, such as passing the washing liquid through a bed of the allulose crystals or by slurrying the separated allulose crystals in a volume of the washing liquid and then subjecting the slurry to a physical separation step such as centrifugation, decantation, membrane separation and/or filtration to recover washed allulose crystals from the washing liquid. Any suitable washing liquid may be utilized, such as water, an organic solvent (e.g., an alcohol, such as ethanol), a blend of water and one or more organic solvents, a blend of two or more organic solvents, and/or an aqueous solution comprised of at least one carbohydrate such as allulose. In one embodiment, the allulose crystals are washed with an allulose syrup or even a recovered mother liquor having a purity (with respect to allulose) that is higher than the purity of the residual mother liquor initially present in the crystals to be washed.

The allulose crystals separated from the mother liquor of a massecuite may be subjected to a drying step to lower the moisture content of the crystals. The drying step may, for example, be carried out subsequent to a washing step or series of washing steps. The drying of the crystals may be performed in a fluidized bed dryer, a rotary dryer, a vacuum dryer or other such apparatus. For example, in the drying step, the allulose crystals may be dried using an air temperature of up to approximately 100° C., preferably no greater than 80° C., over a period of about 20 minutes to about 24 hours, more preferably about 20 minutes to about 6 hours.

The present invention is capable of producing dry, relatively large, free-flowing crystals of allulose at a lower manufacturing cost (due to better utilization of equipment), as compared to previously known allulose crystallization processes. Such larger crystals have a better appearance than small allulose crystals, which often appear powdery or fluffy. Larger crystals have fewer fines, which in turn leads to lower dusting. Fines (i.e., small crystals) can pack into the spaces between large crystals, possibly resulting in poor flow characteristics as well as caking issues. Additionally, small crystals of allulose have greater surface area as compared to large crystals; this leads to faster moisture sorption, which can also contribute to caking. Dry, free-flowing allulose crystals of the type which can be produced economically using the present invention permit handling by a customer (e.g., a food manufacturer) without the need for special handling equipment.

Processes in accordance with the present invention are capable, for example, of producing an allulose crystal product having an average particle size of at least 100 microns, at least 150 microns, at least 200 microns, or at least 250 microns or even larger (e.g., 250 to 350 microns), in various embodiments of the invention. Average particle size may be determined using a laser diffraction particle size analyzer, such as the LS 13 320 model manufactured by Beckman Coulter. According to certain aspects of the invention, less than 25% of the allulose crystal product obtained is smaller than 75 microns in size.

Figure 2:
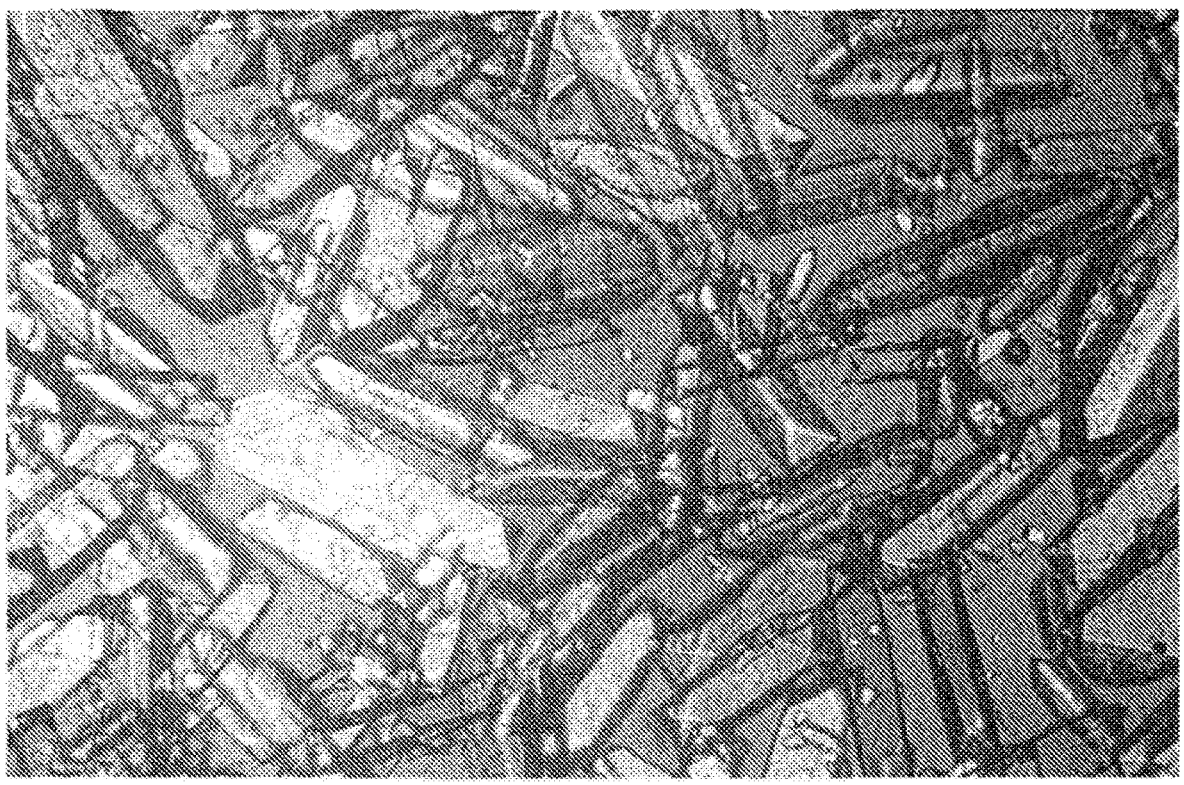
FIG. 2 is a microscopic image of a massecuite containing allulose crystals which has been produced in accordance with an embodiment of the invention.

The present invention can be practiced to obtain allulose crystals having a preferred morphology wherein the allulose crystal has a well-defined three-dimensional shape, rather than the shape of a needle or a flat sheet. FIG. 2 is a microphotographic image of allulose crystals in a massecuite which have such a preferred morphology.

Allulose crystals produced in accordance with at least certain embodiments of the invention may advantageously have, for example, a bulk density greater than 30 lb/ft$^3$ and more preferably greater than 35 lb/ft$^3$.

Uses for Allulose Crystals

Allulose crystals produced by the method of the present invention may be used in a product for human and/or animal consumption. Such use is particularly advantageous in products having a low water content. In some embodiments, the product may be a food product, a beverage product, a pharmaceutical product, a nutritional product, a sports product, or a cosmetic product. For example, when the product is a food product, the food product can be selected from the group consisting of a confectionary product (including a chocolate product), a dessert product, a cereal product, baked goods, frozen dairy products (e.g., ice cream), meats, dairy products (e.g., yogurt), condiments, snack bars, energy bars, nutrition bars, soups, dressings, mixes, prepared foods, baby foods, diet preparations, syrups, food coatings, dried fruit, sauces, gravies, and jams/jellies. In some embodiments, the food product may comprise allulose crystals produced by the method of the present invention in the form of a coating or frosting formed on the surface of the product. Alternatively, when the product is a beverage product, the beverage product can be selected from the group consisting of a carbonated beverage, a non-carbonated beverage, fruit-flavored beverage, fruit juice, tea, milk, coffee, and the like. The food product containing allulose crystals produced in accordance with the invention may also be a tabletop sweetener.

Allulose crystals produced in accordance with the present invention may be used in combination with one or more other food or beverage ingredients, including any of the food and beverage ingredients known in the art. Such additional food and beverage ingredients include, but are not limited to, flavorants, colorants, sweeteners other than allulose (including other carbohydrates such as sucrose, fructose, allose, tagatose and other rare carbohydrates, synthetic high potency sweeteners such as sucralose, acesulfame K, saccharin, aspartame and the like, natural high potency sweeteners such as stevia and monk fruit extract sweeteners and the terpene glycosides present therein, such as steviol glycosides and mogrosides including, but not limited to, rebaudioside A, rebaudioside B, rebaudioside C, rebaudioside D, rebaudioside E, rebaudioside F, rebaudioside G, rebaudioside H, rebaudioside I, rebaudioside J, rebaudioside K, rebaudioside L, rebaudioside M (also known as rebaudioside X), rebaudioside N, rebaudioside O, stevioside, steviolmonoside, steviolbioside, dulcoside A, dulcoside B, rubusoside, glycosylated steviol glycosides, enzyme-modified steviol glycosides, mogroside II A, mogroside II B, 7-oxomogroside II E, 11-oxomogroside A, mogroside III A$_2$, 11-deoxymogroside III, 11-oxymogroside IV A, 7-oxomogroside V, 11-oxomogroside V, mogroside V, mogroside VI and the like and combinations thereof), dietary fibers (including soluble dietary fibers such as soluble corn fiber and polydextrose), acidulants, water, and the like. The allulose crystals may be admixed or blended with such other ingredients in dry form. In other embodiments, the allulose crystals may be coated with one or more other ingredients; for example, a solution containing one or more other ingredients (such as a high potency sweetener, combination of high potency sweeteners, and/or one or more other carbohydrates), may be applied to the allulose crystals by spraying or other such procedure and then dried.

What is claimed:

1. A purified allulose crystal product, wherein the purified allulose crystal product has a purity of at least 90% by dry weight of the crystals, an average particle size of at least 100 microns, and one or more particles smaller than 75 microns in size in less than 25% by dry weight of the purified allulose crystal product.

2. The purified crystal product of claim 1, wherein the purified allulose crystal product has a purity of at least 95% by dry weight of the crystals.

3. The purified crystal product of claim 1, wherein the purified allulose crystal product has a purity of at least 99% by dry weight of the crystals.

4. The purified crystal product of claim 1, wherein the purified allulose crystal product has an average particle size of at least 200 microns.

5. The purified crystal product of claim 1, wherein the purified allulose crystal product has an average particle size of at least 250 microns.

6. The purified crystal product of claim 1, wherein the purified allulose crystal product has an average particle size of from 250 to 350 microns.

7. The purified crystal product of claim 1, wherein the purified allulose crystal product has a bulk density greater than 30 lb/ft$^3$.

8. The purified crystal product of claim 1, wherein the purified allulose crystal product has a bulk density greater than 35 lb/ft$^3$.

9. The purified allulose crystal product of claim 1, wherein crystals in the purified allulose crystal product have a well-defined three-dimensional shape.

10. A tabletop sweetener comprising the purified allulose crystal product of claim 1.

11. A product for human and/or animal consumption comprising the purified allulose crystal product of claim 1 and at least one additional ingredient selected from the group consisting of flavorants, colorants, sweeteners other than allulose, carbohydrates, sucrose, fructose, allose, tagatose, synthetic sweeteners, sucralose, acesulfame K, saccharin, aspartame, natural high potency sweeteners, *stevia* extract sweeteners, monk fruit extract sweeteners, terpene glycosides, steviol glycosides, mogrosides, rebaudioside A, rebaudioside B, rebaudioside C, rebaudioside D, rebaudioside E, rebaudioside F, rebaudioside G, rebaudioside H, rebaudioside I, rebaudioside J, rebaudioside K, rebaudioside L, rebaudioside M, rebaudioside N, rebaudioside O, stevioside, steviolmonoside, steviolbioside, dulcoside A, dulcoside B, rubusoside, glycosylated steviol glycosides, enzyme-modified steviol glycosides, mogroside II A, mogroside II B, 7-oxomogroside II E, 11-oxomogroside A, mogroside III A$_2$, 11-deoxymogroside III, 11-oxymogroside IV; A, 7-oxomogroside V, 11-oxomogroside V, mogroside V, mogroside VI, dietary fibers, soluble dietary fibers, soluble corn fiber, polydextrose, acidulants, water, and mixtures of distinct additional ingredients thereof; and wherein the product for human and/or animal consumption is selected from the group consisting of a food product, a beverage product, a pharmaceutical product, a nutritional product, a sports product, and a cosmetic product.

12. The product for human and/or animal consumption of claim 11, wherein the product is selected from the group consisting of a confectionary product, a chocolate product, a dessert product, a cereal product, baked goods, frozen dairy products, ice cream, meats, dairy products, yogurt, condiments, snack bars, energy bars, nutrition bars, soups, dressings, mixes, prepared foods, baby foods, diet preparations, syrups, food coatings, dried fruit, sauces, gravies, jams, jellies, a carbonated beverage, a non-carbonated beverage, fruit-flavored beverage, fruit juice, tea, milk, and coffee.

13. The product for human and/or animal consumption of claim 11, wherein the product comprises a dry admixture of the purified allulose crystal product and the at least one additional ingredient.

14. The product for human and/or animal consumption of claim 11, wherein the product comprises the purified allulose crystal product coated with the at least one additional ingredient.

15. A massecuite comprising mother liquor and purified allulose crystals, wherein the purified allulose crystals have a purity of at least 90% by dry weight of the purified allulose crystals, an average particle size of at least 100 microns, and one or more particles smaller than 75 microns in size in less than 25% by dry weight of the purified allulose crystals.

16. The massecuite of claim 15, wherein the purified allulose crystals have a purity of at least 95% by dry weight of the crystals.

17. The massecuite of claim 15, wherein the purified allulose crystals have a purity of at least 99% by dry weight of the crystals.

18. The massecuite of claim 15, wherein the purified allulose crystals have an average particle size of at least 200 microns.

19. The massecuite of claim 15, wherein the purified allulose crystals have an average particle size of at least 250 microns.

20. The massecuite of claim 15, wherein the purified allulose crystals have an average particle size of from 250 to 350 microns.

21. The massecuite of claim 15, wherein the purified allulose crystals have a bulk density greater than 30 $lb/ft^3$.

22. The massecuite of claim 15, wherein the purified allulose crystals have a bulk density greater than 35 $lb/ft^3$.

23. The massecuite of claim 15, wherein the purified allulose crystals have a well-defined three-dimensional shape.

* * * * *